United States Patent
Mårtensson et al.

(10) Patent No.: US 10,605,595 B2
(45) Date of Patent: Mar. 31, 2020

(54) BIKING ACTIVITY RECOGNITION THROUGH COMBINATION OF ELECTRIC FIELD SENSING AND ACCELEROMETER

(71) Applicant: Sony Mobile Communications Inc., Tokyo (JP)

(72) Inventors: Linus Mårtensson, Lund (SE); Magnus Midholt, Limhamn (SE); Alexandar Rodzevski, Lund (SE); Henrik Bengtsson, Lund (SE)

(73) Assignee: Sony Corporation, Tokyo (JP)

(*) Notice: Subject to any disclaimer, the term of this patent is extended or adjusted under 35 U.S.C. 154(b) by 1042 days.

(21) Appl. No.: 14/685,710

(22) Filed: Apr. 14, 2015

(65) Prior Publication Data
US 2016/0305776 A1    Oct. 20, 2016

(51) Int. Cl.
*G01B 21/00* (2006.01)
*G01R 29/08* (2006.01)
*G06K 9/00* (2006.01)
*A61B 5/11* (2006.01)
*G01D 21/02* (2006.01)
*A61B 5/00* (2006.01)
*A61B 5/04* (2006.01)
*G01H 3/00* (2006.01)
*G01P 15/00* (2006.01)

(52) U.S. Cl.
CPC .......... *G01B 21/00* (2013.01); *A61B 5/04002* (2013.01); *A61B 5/1118* (2013.01); *A61B 5/681* (2013.01); *G01D 21/02* (2013.01); *G01H 3/00* (2013.01); *G01P 15/00* (2013.01); *G01R 29/08* (2013.01); *G06K 9/00342* (2013.01); *A61B 2562/0219* (2013.01); *A61B 2562/0223* (2013.01)

(58) Field of Classification Search
CPC ........ G01B 21/00; G01R 29/08; G01R 29/12; G01R 29/14; G01P 15/00; G06K 9/00342; G06K 9/00348; G06K 9/00355; G06K 9/00375; G06K 9/00382; G06K 9/00389; G06K 2009/00395; A61B 5/04002; A61B 5/681; A61B 5/1118; A61B 5/1123; A61B 2562/0223; A61B 2562/0219
See application file for complete search history.

(56) References Cited

PUBLICATIONS

Mokaya et al., MARS: A Muscle Activity Recognition System Using Inertial Sensors, Apr. 16-20, 2012, IPSN '12, Beijing, China, pp. 97-98.*

(Continued)

*Primary Examiner* — Toan M Le
(74) *Attorney, Agent, or Firm* — Renner, Otto, Boisselle & Sklar, LLP

(57) ABSTRACT

An apparatus and method for determining a user activity include or define a plurality of baseline signatures, each baseline signature corresponding to a type of user activity and having data formed from a first data representing a varying static electric field and a second data representing motion. Data responsive to a varying static electric field is obtained from a first sensor, and data responsive to motion is obtained from a second sensor. The first data is combined with the second data, and the user activity is identified based on a comparison of the combined first and second data with the plurality of baseline signatures.

20 Claims, 3 Drawing Sheets

(56) References Cited

PUBLICATIONS

Geppert, Marcel, "Smart Environments without cameras: Electrical Field Sensing for Human-Computer Interaction", Ubiquitous Computing Seminar FS2014-Student Report; 2014.
Cohn, Gabe, et al., "An Ultra-Low-Power Human Body Motion Sensor Using Static Electric Field Sensing", UbiComp; Sep. 2012.
https://www.youtube.com/watch?v=IJq_MvwbGNA; Jan. 12, 2013; Relative to screen shot provided for reference.
https://www.youtube.com/watch?v=OIRKCpJWAEg; Mar. 21, 2014; Relative to screen shot provided for reference.
https://www.youtube.com/watch?v=Q4EzGqmDEJ8; Sep. 30, 2012; Relative to screen shot provided for reference.
https://www.youtube.com/watch?v=OLLBPRbu-0A; Mar. 27, 2014; Relative to screen shot provided for reference.

\* cited by examiner

BIKING ACTIVITY RECOGNITION THROUGH COMBINATION OF ELECTRIC FIELD SENSING AND ACCELEROMETER

TECHNICAL FIELD OF THE INVENTION

The technology of the present disclosure relates generally to electronic devices and, more particularly, to techniques for enhancing detection of user activities via an electronic device carried or worn by a user.

BACKGROUND

Electronic devices, such as smart phones, smart watches, wrist bands and the like, can include applications (apps) that enable tracking of physical activities. This can include, for example, distance measurements (e.g., how far did a person walk or run), average speed measurements (e.g., how fast did the person walk or run), heart rate measurements, calories burned, etc.

To detect physical activity, the electronic device typically includes an accelerometer that can detect movement of the electronic device and, thus, of the user. For example, an electronic device in the form of a smart watch may be worn on the user's wrist. As the user performs a physical activity, the user's arms (and thus the electronic device) undergo motion characteristic of the activity. Data corresponding to the characteristic motion can be detected by the accelerometer and analyzed within the electronic device to determine the type of activity as well as any information related to the activity.

A problem with conventional methods for detecting user activity is that they hinge on motion of the part of the body to which the electronic device is attached (worn) or held. Typically, electronic devices are worn on the wrist (smart watch, smart band) or upper arm (e.g., mp3 player, smart phone). Such location of the electronic device can be problematic when the particular activity does not involve motion (or significant motion) of the arm. For example, when bicycling the user's arms are relatively stationary and, thus, detection of physical activity while biking can be difficult.

SUMMARY

To enhance detection of physical activities via an electronic device, the present disclosure describes a detection method and device that employ an accelerometer in combination with a static electric field (EF) sensor. By comparing the data collected from the sensors to data corresponding to predefined activities, the physical activity of the user can be more accurately determined.

According to one aspect of the disclosure, an electronic device includes: a static electric field sensor for detecting a static electric field; at least one other sensor for detecting one of motion or sound; and a control circuit operative to determine an activity performed by a user, the control circuit configured to: obtain first data from the static electric field sensor data corresponding to a static electric field about the electronic device; obtain second data from the at least one other sensor data corresponding to motion of the electronic device; form from the first and second data a characteristic signature; and identify the user activity based on a comparison of the characteristic signature with the plurality of baseline signature.

According to another aspect of the disclosure, a method of determining a user activity includes: defining a plurality of baseline signatures, each baseline signature corresponding to a type of user activity and including data formed from a first data representing a varying static electric field and a second data representing motion; obtaining from a first sensor data responsive to a varying static electric field; obtaining from a second sensor data responsive to motion; forming a characteristic signature from the combination of the first data and the second data; and identifying the user activity based on a comparison of the characteristic signature with the plurality of baseline signatures.

To the accomplishment of the foregoing and the related ends, the device and method comprises the features hereinafter fully described in the specification and particularly pointed out in the claims, the following description and the annexed drawings setting forth in detail certain illustrative embodiments, these being indicative, however, of but several of the various ways in which the principles of the invention may be suitably employed.

Although the various features are described and are illustrated in respective drawings/embodiments, it will be appreciated that features of a given drawing or embodiment may be used in one or more other drawings or embodiments of the invention.

DETAILED DESCRIPTION OF EMBODIMENTS

Figure 1:
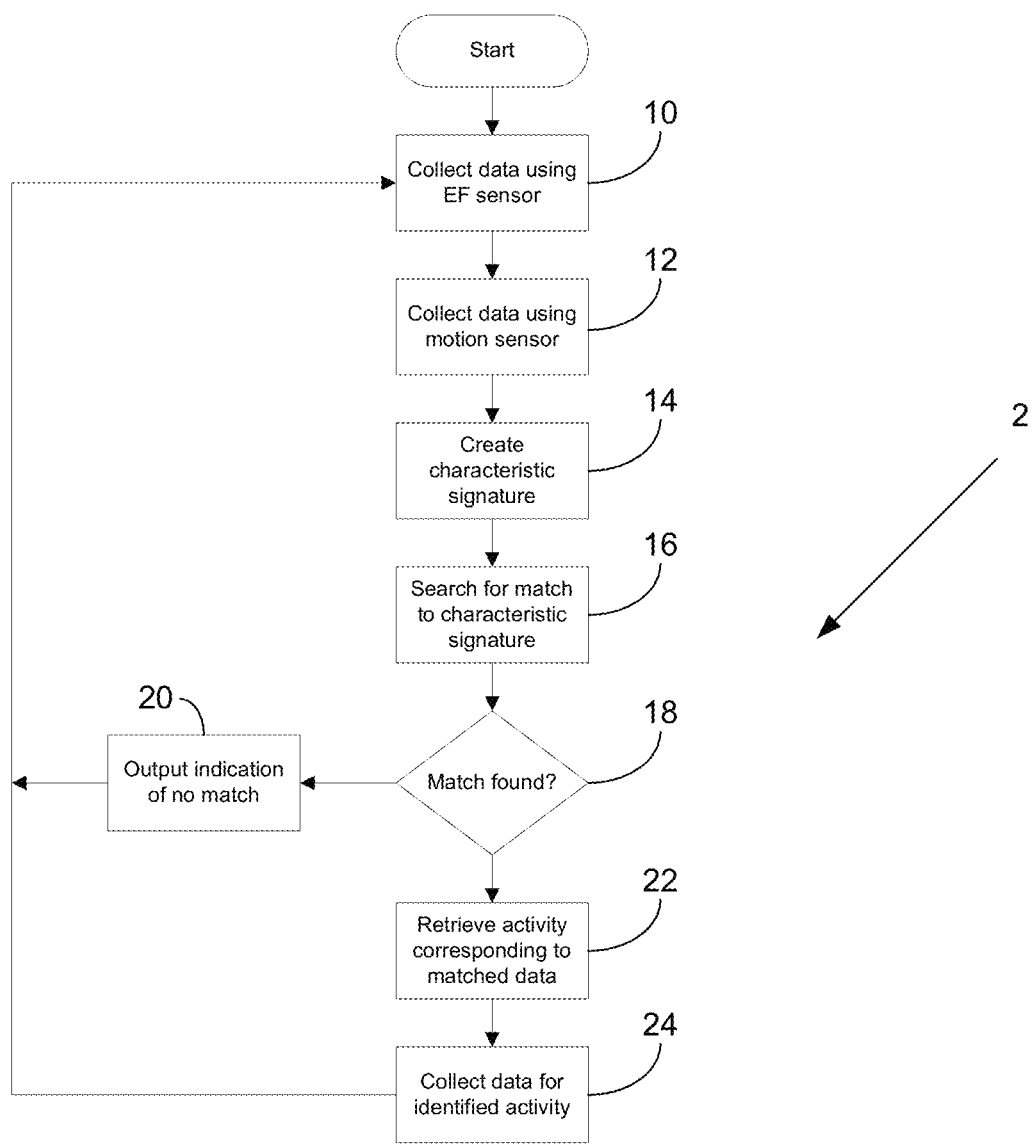
FIG. 1 is a flow chart illustrating an exemplary method of determining a user activity in accordance with the present disclosure.

Embodiments will now be described with reference to the drawings, wherein like reference numerals are used to refer to like elements throughout. It will be understood that the figures are not necessarily to scale. Also, features that are described and/or illustrated with respect to one embodiment may be used in the same way or in a similar way in one or more other embodiments and/or in combination with or instead of the features of the other embodiments.

The present disclosure describes a device and method for determining a user activity. In this regard, a plurality of baseline signatures may be predefined and stored in a database or the like, each baseline signature corresponding to a type of user activity. For example, a first predefined baseline signature may correspond to a user walking, another may correspond to a user running, another may correspond to a user bicycling, another may correspond to a user riding in a motor vehicle, another may correspond to a user flying in an airplane, another may correspond to a user exercising within a home/building, and so forth. The predefined baseline signature may be formed from a plurality of different types of data.

For example, in one embodiment the predetermined baseline signature may be formed from a first data representing a varying static electric field and a second data representing motion. In another embodiment, the baseline signature may be formed from three or more types of data. For example, the baseline signature may be formed from a first data representing a varying static electric field, a second data representing motion, and a third data representing sound.

A characteristic signature for a user activity then is determined based on a plurality of different types of data obtained from the user and/or the user's immediate environment. For example, a first data may be obtained from a first sensor that is responsive to a varying static electric field, and second data may be obtained from a second sensor that is responsive to motion of the user or part of the user. The first data can be combined with the second data to form a characteristic signature, and this characteristic signature can be used as a basis to search the database of predefined baseline signatures. Upon finding a baseline signature that corresponds to the characteristic signature, the user activity associated with the corresponding baseline signature can be identified as the activity being performed by the user.

In one embodiment, the first data corresponds to a static electric field about the user. For example, as the user moves different body parts (e.g., left or right leg, left or right arm, etc.), the interaction of those moving body parts with the ambient static electric field varies. Such variation in the static electric field can be detected by the static electric field sensor and used to form at least part of the characteristic signature.

In another embodiment, the first data corresponds to firing of a vehicle ignition system. For example, internal combustion engines have electronics that control firing of each spark plug. As engine speed varies, the firing of the spark plugs also varies. Such firing can be detected by the static electric field sensor, which when combined with data produced by an accelerometer or other sensor can form a characteristic signature of a user riding in a motor vehicle.

In yet another embodiment, the first data corresponds to an electrical frequency of a power source. For example, when the electronic device is within the confines of a house or other structure, electrical power within the house/structure can be detected by the static electric field sensor. Such electrical power may be an A/C power source operating at 50 or 60 Hz. Variations in the static electric field due to the electric power can be used to form a characteristic signature of a user inside a house/structure.

Variations in the static electric field may also be used to identify the user is in an aircraft. More particularly, power systems of an aircraft have a signature distinct from other power systems. Influences of the electric power system on the static electric field about the user can be collected via the static electric field sensor and used to form a characteristic signature corresponding to the user being in an aircraft.

With respect to the second type of data, at least one of an accelerometer, a gyroscope or a magnetometer may be used as the sensor for collecting the second data. As noted above such second data can be fused (also referred to as sensor fusion) with the first data to form a characteristic signature that can be used to determine an activity of the user.

In yet another embodiment, sound data may be used to form the characteristic signature. For example, bicycling may produce sounds that are unique to such activity. Such sounds can include, for example, the sound produced by the chain and sprockets, shifting of gears (if a multi-speed bicycle), the sound of pedals, the sound of brakes, the sound produced by the wheels/spokes cutting through the air, etc. Similarly, when in an aircraft the sound within the cabin is unique to the aircraft (e.g., a drone). A microphone of the electronic device can collect such sound data, which then can be combined with the static electric field sensor data and/or accelerometer data to further define the characteristic signature and provide enhanced data regarding the user activity.

Referring initially to FIG. 1, illustrated is a flow diagram that depicts an exemplary method of detecting user activity via an electronic device. Although the method descriptions and flow chart may show specific orders of executing steps, the order of executing the steps may be changed relative to the order described. Also, two or more steps described in succession may be executed concurrently or with partial concurrence. One or more of the described or illustrated steps may be omitted.

The exemplary method of FIG. 1 may be implemented using coded instructions (e.g., computer readable instructions) stored on one or more non-transitory computer readable media such as flash memory, read-only memory (ROM), random-access memory (RAM), cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. Typical non-transitory computer readable media include electronic memory devices, magnetic memory devices and optical memory devices. The method may be executed by an electronic device. In one embodiment, to carry out the method, the logical instructions embodying the method are executed by a processor of the electronic device. Alternatively, the method may be at least partially implemented in hardware of the electronic device (e.g., an application-specific integrated circuit (ASIC) or the like.

The method may begin at step 10, where first data is collected using a static electric field sensor. Static electric field sensors operate by detecting changes in the static electric field around a person. More particularly, the sensor relies on static (DC) fields present around the body and measures variations in the static fields. In this regard, the body of the user is capacitively coupled to a local ground plane of the sensor and to the environment, while the local ground plane of the sensor is capacitively coupled to the environment. By measuring the voltage between the local ground plane of the sensor and the body, one can infer motion of the body/body part. Static electric field sensors are well known in the art and thus further details of such sensors are omitted for sake of brevity.

Next at step 12 second data is collected using a second sensor, different from the static electric field sensor. The sensor, for example, may be one of an accelerometer, a gyroscope and/or a magnetometer. Other sensors may be used depending on the specific application. Collection of the second data in step 12 may occur concurrently with collection of the first data in step 10. In other words, data collection via the first (static electric field) sensor and data collection via the second sensor may occur simultaneously or substantially simultaneously.

At step 14, the first and second data may be combined to form a characteristic signature corresponding to the user activity. As used herein, the term "characteristic signature" is defined as a combination of a plurality of different types of data collected over time. For example, and with reference to FIG. 2, a characteristic signature 26 may be a data stream defined by static electric field data 26a, acceleration data 26b, sound data 26c, or any other data that may be captured during an activity. The different types of data, which may be collected using different types of sensors, are combined to form a data stream that defines the characteristic signature, where different types of data corresponding to the same instants in time may be linked together.

The time period t over which the characteristic signature is derived may be short (e.g., an instant in time) so as to form a snapshot of the collected data. Alternatively or additionally, the time t over which the characteristic signature is derived may be extended (t spans a time greater than an instant in time) to form a data stream (e.g., a continuous data stream over a time period t). In one embodiment the characteristic signature is represented as a three-dimensional map.

Referring back to FIG. 1, at step 16 the characteristic signature is used as the basis for searching a data store, such as a database accessible by the electronic device, the database including a plurality of predefined baseline signatures. Each predefined baseline signature stored in the database may correspond to a particular type of activity, e.g., running, bicycling, etc. For example, each baseline signature may have associated therewith the particular activity performed to create the baseline signature. The activity for each baseline signature may be stored in the database and associated with the corresponding signature.

In searching the database for a baseline signature that corresponds to the characteristic signature, a comparison of the respective signatures may be performed. The comparison may include determining if there are deviations in amplitude and/or frequency between the respective signatures, similarities and/or differences in locations of signature events (e.g., acceleration events and/or electric field events that do or do not occur at specific intervals), similarities and/or differences in harmonic frequencies, etc.

If at step 18 it is determined that the characteristic signature does not match or otherwise correspond to a baseline signature stored in the database, then the method moves to step 20 where a message is generated indicating the system could not determine the activity. Such message may be output on a display of the electronic device and may or may not include an audible alarm. Additionally or alternatively, the message may be stored in an application log file or other file for later retrieval and/or analysis. The method then moves back to step 10 and repeats.

Moving back to step 18, if it is determined that the characteristic signature does match or otherwise correspond to a baseline signature stored in the database, then the method moves to step 22 where the activity associated with the matching baseline signature is retrieved from the database. In this manner, it can accurately be determined which activity is performed by the user.

At step 24, additional data may be collected and associated with the determined activity. For example, distance information may be calculated based on data provided by the static electric field sensor and/or accelerometer. Similarly, energy consumption (e.g., calories) consumed for the activity also may be calculated. As will be appreciated, other information may be calculated as specified by one or more applications and/or user input. Upon collecting and/or processing the data, the method moves back to step 10 and repeats.

Figure 3:
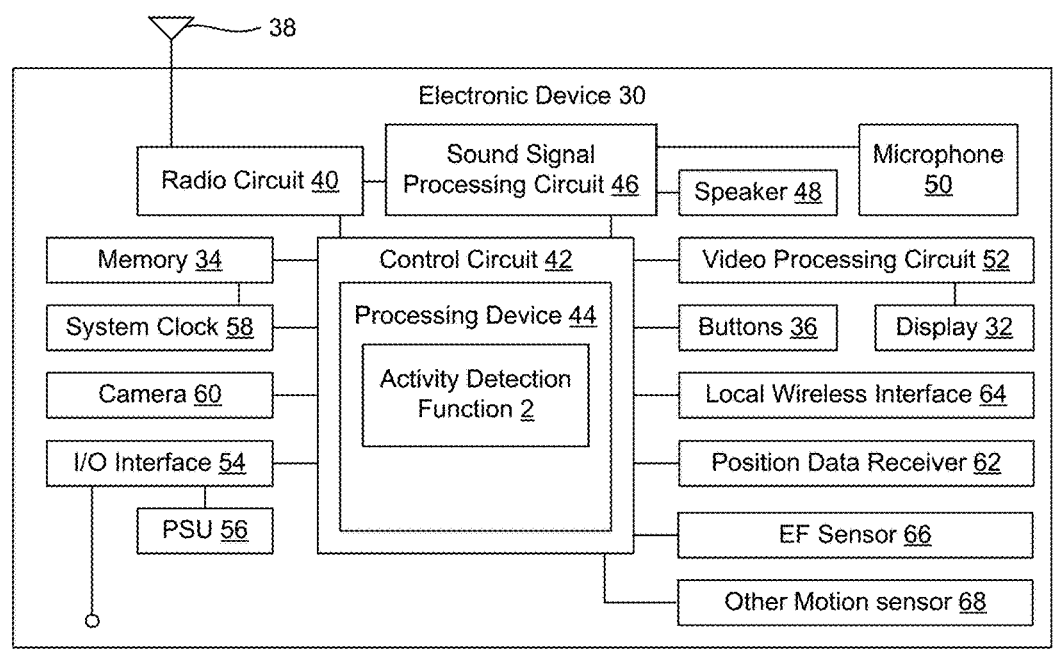
FIG. 3 is a schematic block diagram of the electronic device including an activity detection function in accordance with the present disclosure.

The above-described method may be performed by an electronic device 30, an example of which is illustrated in FIG. 3. The electronic device 30 may be any type of electronic device in which it is desired to limit the peak current draw from batteries of the electronic device, examples of which include a smart watch, a head set, a media player, a gaming device, a communicator, a portable communication apparatus, a bracelet, visors, a phone attached to the arm, a ring, etc.

Figure 2:
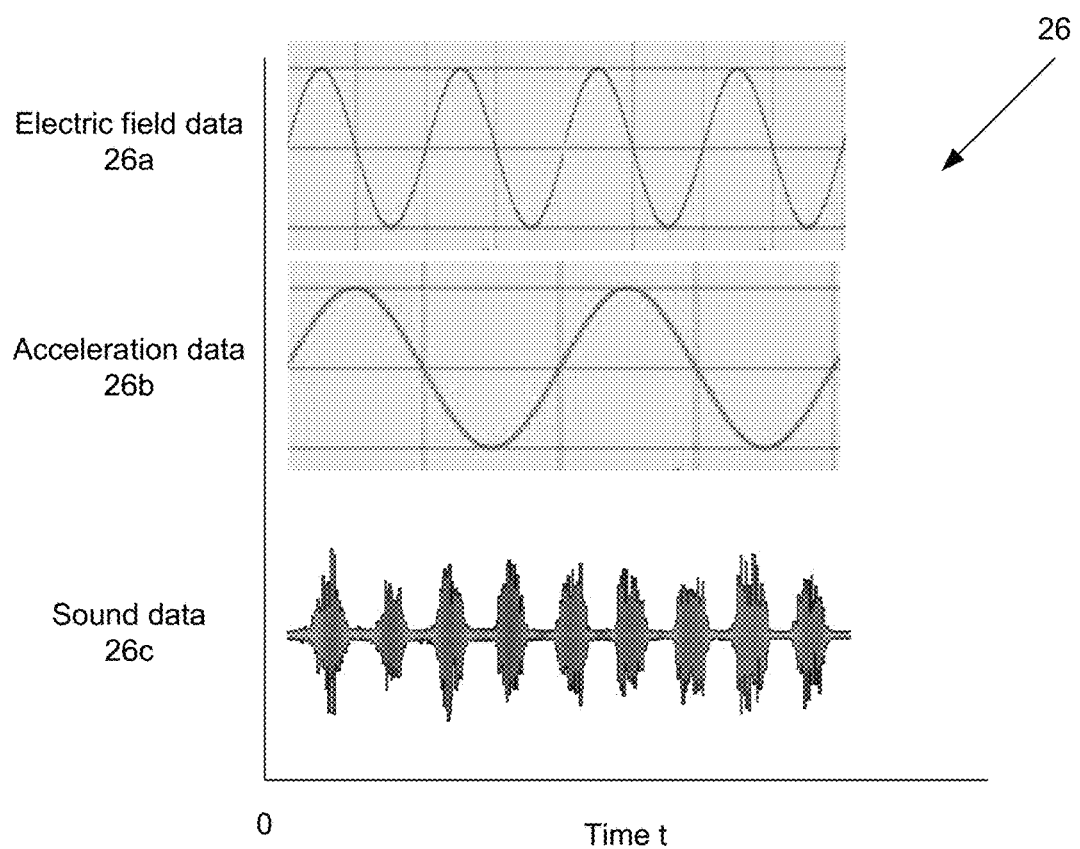
FIG. 2 is a graphical representation of the components of an exemplary characteristic signature in accordance with the present disclosure.

The electronic device 30 includes the activity detection function 2 that is configured to determine an activity performed by a user as described with respect to FIGS. 1-2.

The electronic device 30 may include a display 32. The display 32 displays information to a user such as operating state, time, telephone numbers, contact information, various menus, etc., that enable the user to utilize the various features of the electronic device 30. The display 32 also may be used to visually display content received by the electronic device 30 and/or retrieved from a memory 34 of the electronic device 30. The display 32 may be used to present images, video and other graphics to the user, such as photographs, mobile television content, Internet pages, and video associated with games.

Buttons 36 provide for a variety of user input operations, and in an electronic device embodied as a smart watch may be arranged along a side or edge of the smart watch. For example, the buttons 36 may include buttons for allowing entry of information, special function buttons (e.g., one or more of a call send and answer button, multimedia playback control buttons, a camera shutter button, etc.), navigation and select buttons or a pointing device, and so forth. Buttons or button-like functionality also may be embodied as a touch screen associated with the display 32. Also, the display 32 and buttons 36 may be used in conjunction with one another to implement soft key functionality.

The electronic device 30 includes communications circuitry that enables the electronic device 30 to establish communications with another device. Communications may include calls, data transfers, and the like. Calls may take any suitable form such as, but not limited to, voice calls and video calls. The calls may be carried out over a cellular circuit-switched network or may be in the form of a voice over Internet Protocol (VoIP) call that is established over a packet-switched capability of a cellular network or over an alternative packet-switched network (e.g., a network compatible with IEEE 802.11, which is commonly referred to as WiFi, or a network compatible with IEEE 802.16, which is commonly referred to as WiMAX), for example. Data transfers may include, but are not limited to, receiving streaming content (e.g., streaming audio, streaming video, etc.), receiving data feeds (e.g., pushed data, podcasts, really simple syndication (RSS) data feeds data feeds), downloading and/or uploading data (e.g., image files, video files, audio files, ring tones, Internet content, etc.), receiving or sending messages (e.g., text messages, instant messages, electronic mail messages, multimedia messages), and so forth. This data may be processed by the electronic device 30, including storing the data in the memory 34, executing applications to allow user interaction with the data, displaying video and/or image content associated with the data, outputting audio sounds associated with the data, and so forth.

In the exemplary embodiment, the communications circuitry may include an antenna 38 coupled to a radio circuit 40. The radio circuit 40 includes a radio frequency transmitter and receiver for transmitting and receiving signals via the antenna 38.

The radio circuit 40 may be configured to operate in a mobile communications system. Radio circuit 40 types for interaction with a mobile radio network and/or broadcasting network include, but are not limited to, global system for mobile communications (GSM), code division multiple access (CDMA), wideband CDMA (WCDMA), general packet radio service (GPRS), WiFi, WiMAX, digital video broadcasting-handheld (DVB-H), integrated services digital broadcasting (ISDB), high speed packet access (HSPA), etc., as well as advanced versions of these standards or any other appropriate standard. It will be appreciated that the electronic device 30 may be capable of communicating using more than one standard. Therefore, the antenna 38 and the radio circuit 40 may represent one or more than one radio transceiver.

The electronic device 30 may include a primary control circuit 42 that is configured to carry out overall control of the functions and operations of the electronic device 30. The control circuit 42 may include a processing device 44, such as a central processing unit (CPU), microcontroller or microprocessor. The processing device 44 executes code stored in a memory (not shown) within the control circuit 34 and/or in a separate memory, such as the memory 34, in order to carry out operation of the electronic device 30. For instance, the processing device 44 may execute code that implements the activity detection function 2. The memory 34 may be, for example, one or more of a buffer, a flash memory, a hard drive, a removable media, a volatile memory, a non-volatile memory, a random access memory (RAM), or other suitable device. In a typical arrangement, the memory 34 may include a non-volatile memory for long term data storage and a volatile memory that functions as system memory for the control circuit 42. The memory 34 may exchange data with the control circuit 42 over a data bus. Accompanying control lines and an address bus between the memory 34 and the control circuit 42 also may be present.

The electronic device 30 may further include a sound signal processing circuit 46 for processing audio signals transmitted by and received from the radio circuit 40. Coupled to the sound processing circuit 46 are a speaker 48 and a microphone 50 that enable a user to listen and speak via the electronic device 30. The radio circuit 40 and sound processing circuit 44 are each coupled to the control circuit 42 so as to carry out overall operation. Audio data may be passed from the control circuit 42 to the sound signal processing circuit 46 for playback to the user. The audio data may include, for example, audio data from an audio file stored by the memory 34 and retrieved by the control circuit 42, or received audio data such as in the form of voice communications or streaming audio data from a mobile radio service. The sound processing circuit 44 may include any appropriate buffers, decoders, amplifiers and so forth.

The display 32 may be coupled to the control circuit 42 by a video processing circuit 52 that converts video data to a video signal used to drive the display 32. The video processing circuit 52 may include any appropriate buffers, decoders, video data processors and so forth. The video data may be generated by the control circuit 42, retrieved from a video file that is stored in the memory 34, derived from an incoming video data stream that is received by the radio circuit 40 or obtained by any other suitable method.

The electronic device 30 may further include one or more input/output (I/O) interface(s) 54. The I/O interface(s) 54 may be in the form of typical smart watch I/O interfaces and may include one or more electrical connectors. The I/O interfaces 54 may form one or more data ports for connecting the electronic device 30 to another device (e.g., a computer) or an accessory (e.g., a personal hands free (PHF) device) via a cable. Further, operating power may be received over the I/O interface(s) 54 and power to charge a battery of a power supply unit (PSU) 56 within the electronic device 30 may be received over the I/O interface(s) 54. The PSU 56 may supply power to operate the electronic device 30 in the absence of an external power source.

The electronic device 30 also may include various other components. For instance, a system clock 58 may clock components such as the control circuit 42 and the memory 34. A camera 60 may be present for taking digital pictures and/or movies. Image and/or video files corresponding to the pictures and/or movies may be stored in the memory 34. A position data receiver 62, such as a global positioning system (GPS) receiver, Galileo satellite system receiver or the like, may be involved in determining the position of the electronic device 30. A local wireless interface 64, such as an infrared transceiver and/or an RF transceiver (e.g., a Bluetooth chipset) may be used to establish communication with a nearby device, such as an accessory (e.g., a PHF device), another mobile radio terminal, a computer or another device.

The electronic device 30 also includes a static electric field sensor 66. The static electric field sensor 66 detects variations in the static electric field about the electronic device 30 and/or a user of the electronic device 30. The static electric field sensor 66 may be a conventional static electric field sensor known in the art. The electronic device 30 may also include a motion sensor 68, such as an accelerometer, gyroscope and/or magnetometer. As described herein, data from the static electric field sensor 66, the other sensor 68 and/or the microphone 50 may be used to create a characteristic signature for a user activity.

Figure 4A:
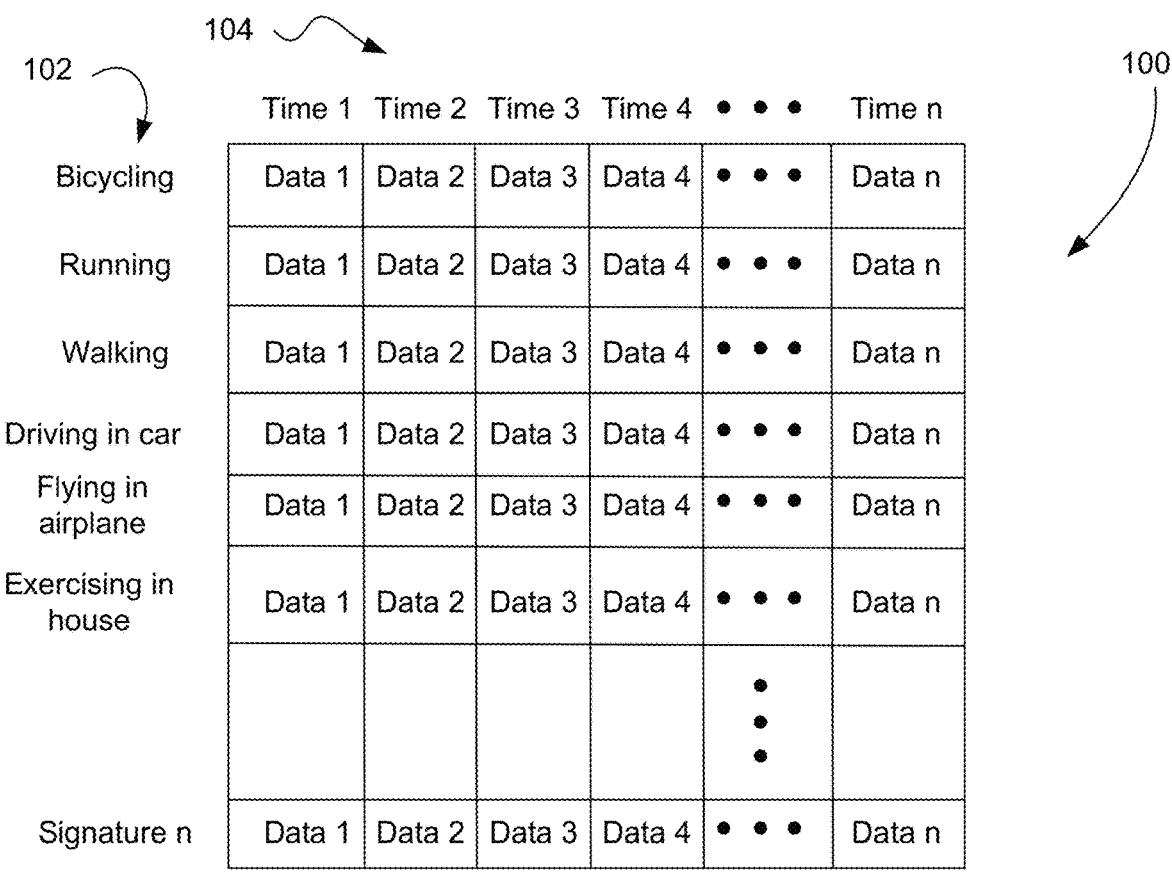
FIG. 4A illustrates an exemplary database that may be used to store one or more signatures in accordance with the present disclosure.
Figure 4B:
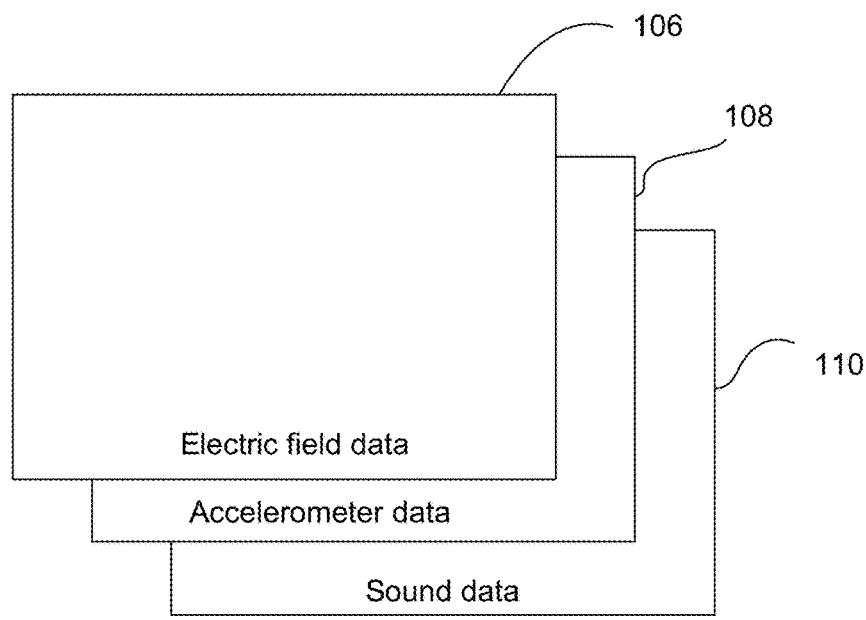
FIG. 4B illustrates the database of FIG. 4A as a multi-dimensional database/historian.

Moving now to FIG. 4, illustrated is an exemplary means for storing one or more baseline signatures in accordance with the present disclosure. The exemplary storage means is illustrated as a simple database 100 having a row and column format. It will be appreciated, however, that any conventional methodology for storing a plurality of data may be used without departing from the scope of the invention.

The exemplary database 100 (e.g., a historian that stores streams of data) includes a plurality of rows 102, each row corresponding to one baseline signature. Thus, for example, a first row may store baseline signature data corresponding to bicycling, a second row may store baseline signature data corresponding to running, a third row may store baseline signature data corresponding to walking, a fourth row may store baseline signature data corresponding to driving in a vehicle, and so on.

The exemplary database 100 also includes a plurality of columns 104, each column corresponding to a particular data entry. For example, baseline signature data may be stored based on a time stamp provided to each data point of the signature. In this regard, time (t) may begin at 0 (t=0), which corresponds to the moment at which collection of the data is initiated. Subsequent data points then may be provided with a time stamp relative to t=0 based on a sampling period used to collect the data, and stored in the column corresponding to the time stamp. The number of data points stored for each signature as well as the number of signatures is limited only by the hardware of the storage medium (e.g., processing power and physical memory).

The exemplary database may be multidimensional. For example, and with reference to FIG. 4B, the database may have a first dimension 106 corresponding to static electric field data, a second dimension 108 corresponding to acceleration data, a third dimension 110 corresponding to sound data, and so on. The first, second and third dimensions may be correlated to one another based on time.

In one embodiment, the database 100 is stored within the electronic device 30, such as within memory 34 or other memory of the electronic device. In another embodiment, the database 100 is stored remote from the electronic device 30. For example, the database 100 may be stored in a server (not shown) or other storage device that is accessible by the electronic device 30 via a network connection or other communication interface. The communication interface may include wired and/or wireless technologies. In yet another embodiment, the database may reside on the electronic device 30, and be off-loaded to the server when network access is available.

Although certain embodiments have been shown and described, it is understood that equivalents and modifications falling within the scope of the appended claims will occur to others who are skilled in the art upon the reading and understanding of this specification.

What is claimed is:

1. An electronic device, comprising:
    a static electric field sensor for detecting a static electric field;
    at least one other sensor for detecting one of motion or sound; and
    a control circuit operative to determine an activity performed by a user, the control circuit configured to:
       obtain first data from the static electric field sensor data corresponding to a static electric field about the electronic device;
       obtain second data from the at least one other sensor data corresponding to motion of the electronic device;
       form from the first and second data a characteristic signature; and
       identify the user activity based on a comparison of the characteristic signature with a plurality of baseline signatures.

2. The electronic device according to claim 1, further comprising a database for storing the plurality of baseline signatures.

3. The electronic device according to claim 2, wherein the database includes a plurality of baseline signatures, at least one baseline signature of the plurality of baseline signatures corresponding at least in part to a static electric field about the user.

4. The electronic device according to claim 2, wherein the database includes a plurality of baseline signatures, at least one baseline signature of the plurality of baseline signatures corresponding at least in part to firing of a vehicle ignition system.

5. The electronic device according to claim 2, wherein the database includes a plurality of baseline signatures, at least one baseline signature of the plurality of baseline signatures corresponding at least in part to an electrical frequency of a power source.

6. The electronic device according to claim 5, wherein the at least one baseline signature of the plurality of baseline signatures corresponding at least in part to the electrical frequency of a power source includes a baseline signature corresponding to an A/C power source operating at 50 or 60 Hz.

7. The electronic device according to claim 1, wherein at least one of the plurality of baseline signatures corresponds to at least one of walking, running, biking, riding in a motor vehicle, or flying in an airplane.

8. The electronic device according to claim 1, wherein the at least one other sensor comprises at least one of an accelerometer, a gyroscope or a magnetometer.

9. An electronic device, comprising:
    a static electric field sensor for detecting a static electric field;
    at least one other sensor for detecting one of motion or sound;
    a sound capture device; and
    a control circuit operative to determine an activity performed by a user, the control circuit configured to:
       obtain first data from the static electric field sensor corresponding to a static electric field about the electronic device;
       obtain second data from the at least one other sensor corresponding to motion of the electronic device;
       form from the first and second data a characteristic signature;
       identify the user activity based on a comparison of the characteristic signature with a plurality of baseline signatures;
       obtain third data from the sound capture device, the third data corresponding to sound in an environment of the electronic device; and
       form the characteristic signature from the first, second data and third data.

10. The electronic device according to claim 9, wherein the database includes a plurality of baseline signatures, at least one baseline signature of the plurality of baseline signatures corresponding at least in part to sound created by pedaling a bicycle or sound within a cabin of an aircraft.

11. A method of determining a user activity, comprising:
    defining a plurality of baseline signatures, each baseline signature corresponding to a type of user activity and including data formed from a first data representing a varying static electric field and a second data representing motion;
    obtaining from a first sensor data responsive to a varying static electric field;
    obtaining from a second sensor data responsive to motion;
    forming a characteristic signature from the combination of the first data and the second data; and
    identifying the user activity based on a comparison of the characteristic signature with the plurality of baseline signatures.

12. The method according to claim 11, wherein the first data corresponds to a static electric field about the user.

13. The method according to claim 11, wherein the first data corresponds to firing of a vehicle ignition system.

14. The method according to claim 11, wherein the first data corresponds to an electrical frequency of a power source.

15. The method according to claim 14, wherein the power source is an A/C power source operating at 50 or 60 Hz.

16. The method according to claim 11, wherein obtaining from the first sensor includes using an electric field sensor as the first sensor.

17. The method according to claim 11, wherein obtaining from the second sensor includes using at least one of an accelerometer, a gyroscope or a magnetometer as the second sensor.

18. The method according to claim 11, wherein the activity comprises at least one of walking, running, biking, riding in a motor vehicle, or flying in an airplane.

19. The method according to claim 11, further comprising:
    further forming the each baseline signature from sound data;
    obtaining from a third sensor ambient sound data; and
    combining the first and second data with the third data.

20. The method according to claim 19, wherein the sound data is characteristic of at least one of sound created by pedaling a bicycle or sound within a cabin of an aircraft.

* * * * *